(12) United States Patent
Daly et al.

(10) Patent No.: US 7,087,411 B2
(45) Date of Patent: *Aug. 8, 2006

(54) FUSION PROTEIN CAPABLE OF BINDING VEGF

(75) Inventors: Thomas J. Daly, New City, NY (US); James P. Fandl, LaGrangeville, NY (US); Nicholas J. Papadopoulos, LaGrangeville, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 288 days.

This patent is subject to a terminal disclaimer.

(21) Appl. No.: 10/609,775

(22) Filed: Jun. 30, 2003

(65) Prior Publication Data
US 2004/0014667 A1    Jan. 22, 2004

Related U.S. Application Data

(63) Continuation-in-part of application No. 10/009,852, filed as application No. PCT/US00/14142 on May 23, 2000.

(60) Provisional application No. 60/138,133, filed on Jun. 8, 1999.

(51) Int. Cl.
| | |
|---|---|
| *C07H 21/04* | (2006.01) |
| *C07K 14/71* | (2006.01) |
| *C12N 15/12* | (2006.01) |
| *C12P 21/02* | (2006.01) |
| *A61K 38/16* | (2006.01) |

(52) U.S. Cl. .............. 435/69.7; 530/350; 530/399; 435/252.3; 435/320.1; 536/23.4

(58) Field of Classification Search ............... None
See application file for complete search history.

(56) References Cited

U.S. PATENT DOCUMENTS

| | | |
|---|---|---|
| 5,851,999 A | 12/1998 | Ullrich et al. |
| 6,011,003 A | 1/2000 | Charnock-Jones |
| 6,100,071 A * | 8/2000 | Davis-Smyth et al. ..... 435/69.7 |
| 6,270,993 B1 | 8/2001 | Shibuya |

FOREIGN PATENT DOCUMENTS

| | | |
|---|---|---|
| WO | WO 97/44453 | 11/1997 |
| WO | WO 98/13071 | 2/1998 |

OTHER PUBLICATIONS

Wells (Sep. 18, 1990) Biochemistry 29(37): 8509-8517.*
Ngo et al. (Mar. 2, 1995) "The Protein Folding Problem and Tertiary Structure Prediction, Chapter 14: Computational Complexity Protein Structure Prediction, and the Levinthal Paradox" pp. 492-495.*
Bork (2000) Genome Research 10:398-400.*
Skolnick and Fetrow (2000) Trends in Biotech. 18(1):34-39.*
Doerks et al. (Jun. 1998) Trends in Genetics 14(6): 248-250.*
Smith and Zhang (Nov. 1997) Nature Biotechnology 15:1222-1223.*
Brenner (Apr. 1999) Trends in Genetics 15(4): 132-133.*
Bork and Bairoch (Oct. 1996) Trends in Genetics 12(10): 425-427.*
Wang et al. (1999) Nuc Acids Res. 27: 4609-4618.*
Kaufman et al (1999) Blood 94: 3178-3184.*
Wigley et al. (1994) Reprod Fert Dev 6: 585-588.*
Phillips, A., J Pharm Pharmacology 53: 1169-1174, 2001.*
Ashkenazi et al, 1995. Methods: A companion to Methods in Enzymology. 8: 104-115.*
Holash, J., et al., (2002) PNAS, 99(17):11393-11398.
Heidaran, M.A., et al., (1990) J. Biol. Chem. 265(31):18741-18744.
Cunningham, S.A., et al., (1997) Biochem. Biophys. Res. Comm. 231:596-599.
Fuh, G., et al., (1998). J. Biol. Chem. 273(18):11197-11204.
Wiesmann, C., et al., (1997) Cell, 91:695-704.
Barleon, B., et al., (1997) J. Biol. Chem. 272(16):10382-10388.
Davis-Smyth, T., et al., (1998) J. Biol. Chem. 273(6):3216-3222.

* cited by examiner

*Primary Examiner*—Janet L. Andres
*Assistant Examiner*—Zachary Howard
(74) *Attorney, Agent, or Firm*—Valeta Gregg, Esq.

(57) ABSTRACT

Nucleic acid molecules and multimeric proteins capable of binding vascular endothelial growth factor (VEGF). VEGF mini-traps are disclosed which are therapeutically useful for treating VEGF-associated conditions and diseases, and are specifically designed for local administration to specific organs, tissues, and/or cells.

16 Claims, 5 Drawing Sheets

VEGF TRAP with a thrombin cleavage site between FLK1 and Fc domains

Generation of Non-Fc tagged dimeric / monomeric VEGF-Trap

Proteolytic cleavage generates several species depending on location of cleavage site, leading to monomer vs dimer forms non-reducing reducing

US 7,087,411 B2

FUSION PROTEIN CAPABLE OF BINDING VEGF

CROSS-REFERENCE TO RELATED APPLICATIONS

The application is a continuation-in-part of U.S. Ser. No. 10/009,852 filed 6 Dec 2001, which is a national application of PCT/US00/14142 filed 23 May 2000, which claims priority of U.S. Provisional Application No. 60/138,133, filed on Jun. 8, 1999, which applications are herein specifically incorporated by reference in their entireties.

BACKGROUND OF THE INVENTION

Field of the Invention

The invention encompasses fusion proteins capable of binding vascular endothelial cell growth factor (VEGF), VEGF family members, and splice variants with specifically desirable characteristics, as well as therapeutic methods of use.

BRIEF SUMMARY OF THE INVENTION

In a first aspect, the invention features an isolated nucleic acid molecule encoding a fusion polypeptide consisting of components $(R1R2)_X$ and/or $(R1R3)_Y$, wherein R1 is vascular endothelial cell growth factor (VEGF) receptor component Ig domain 2 of Flt-1 (Flt1D2), R2 is VEGF receptor component Ig domain 3 of Flk-1 (Flk1D3), R3 is VEGF receptor component Ig domain 3 of Flt-4 (Flt1D3 or R3), and wherein $X \geq 1$ and $Y \geq 1$.

In a related second aspect, the invention features a monomeric VEGF trap consisting of VEGF receptor components $(R1R2)_X$ and/or $(R1R3)_Y$ wherein $X \geq 1$, $Y \geq 1$, and R1, R2, and R3 are as defined above. The VEGF receptor components R1, R2, and R3, may be connected directly to each other or connected via one or more spacer sequences. In one specific embodiment, the monomeric VEGF trap is $(R1R2)_X$, were X=2. In a more specific embodiment, the monomeric VEGF trap is SEQ ID NO:24, or a functionally equivalent amino acid variant thereof. The invention encompasses a monomeric VEGF trap consisting essentially of VEGF receptor components $(R1R2)_X$ and/or $(R1R3)_Y$ and functionally equivalent amino acid variants thereof.

In a third aspect, the invention features an isolated nucleic acid molecule encoding a fusion polypeptide consisting of VEGF receptor components $(R1R2)_X$ and/or $(R1R3)_Y$, and a multimerizing component (MC), and MC is selected from the group consisting of (i) a multimerizing component comprising a cleavable region (C-region), (ii) a truncated multimerizing component, (iii) an amino acid sequence between 1 to about 200 amino acids in length having at least one cysteine residue, (iv) a leucine zipper, (v) a helix loop motif, and (vi) a coil-coil motif. Further encompassed are fusion polypeptides consisting essentially of $(R1R2)_X$ and/or $(R1R3)_Y$, and MC.

In a fourth aspect, the invention features a fusion polypeptide comprising VEGF receptor components $(R1R2)_X$ and/or $(R1R3)_Y$, and MC, wherein MC is selected from the group consisting of (i) a multimerizing component comprising a cleavable region (C-region), (ii) a truncated MC, (iii) an amino acid sequence between 1 to about 200 amino acids in length having at least one cysteine residue, (iv) a leucine zipper, (v) a helix loop motif, and (vi) a coil-coil motif. The receptor components may be arranged in different orders, for example, $(R1R2)_X$-MC; $(R1R2)_X$-MC-$(R1R2)_X$; MC-$(R2R1)_X$, etc. The components of the fusion polypeptide may be connected directly to each other, or connected via a spacer sequence.

In a fifth aspect, the invention features a VEGF trap, comprising a multimer of two or more fusion polypeptides consisting of VEGF receptor components $(R1R2)_X$ and/or $(R1R3)_Y$, and MC, wherein the MC domain of a fusion protein comprises a C-region. The C-region may be naturally occurring or artificial, and may occur at any point within the multimerizing component, and functions to allow cleavage of a parent MC to a truncated MC. A VEGF trap composed of two or more fusion proteins having at least one truncated MC is termed a "truncated mini-trap."

The C-region may be created in MC by insertion, deletion, or mutation, such that an enzymatically or chemically cleavable site is created. The C-region may be created in any MC and at any position within the MC; preferably, the C-region is created in a full length Fc domain, or a fragment thereof, or a $C_H3$ domain. The C-region may be a site cleavable by an enzyme, such as, thrombin, ficin, pepsin, matrilysin, or prolidase or cleavable chemically by, for example, formic acid or $CuCl_2$.

In a sixth related aspect, the invention features a truncated VEGF mini-trap which is a multimeric protein comprising two or more fusion proteins consisting of $(R1R2)_X$ and/or $(R1R3)_Y$ and a multimerizing component which is a truncated by cleavage from a parent MC comprising a C-region (tMC). The truncated mini-trap of the invention is formed by subjecting a parent trap having C-region-containing MC to conditions under which one or more of the C-region-containing MCs is (are) cleaved. A depiction of full and partial cleavage of a parent trap is shown in FIG. 4 for a parent trap in which a thrombin cleavage region was introduced after the second cysteine residue of an Fc domain (FIG. 2). In a preferred embodiment, the truncated VEGF mini-trap is dimeric, formed by subjecting a parent trap having C-region-containing MCs to conditions under which one or more of the C-region-containing MCs is (are) cleaved, wherein the C-region is C-terminal to one or more cysteine residues in the parent MC. In another embodiment, the truncated VEGF mini-trap is monomeric, formed by subjecting a parent trap having C-region-containing MCs to conditions under which one or more of the C-region-containing MCs is (are) cleaved, wherein the C-region is N-terminal to one or more cysteine residues in the parent MC. In this embodiment, the MC regions containing the disulfide bonds holding two or more fusion proteins are removed, and the mini-trap consists of $(R1R2)_X$, as shown in FIG. 3.

In a seventh aspect, the invention features a fusion polypeptide consisting of VEGF receptor components $(R1R2)_X$ and/or $(R1R3)_Y$ and a MC, wherein the MC is an amino acid sequence between 1 to about 200 amino acids in length comprising at least one cysteine residue, wherein the at least one cysteine residue is capable of forming a disulfide bond with a cysteine residue present in the MC of another fusion polypeptide (cMC).

In an eighth aspect, the invention features a VEGF mini-trap, comprising a multimer of two or more fusion polypeptides consisting of $(R1R2)_X$ and/or $(R1R3)_Y$ and a cMC. In a more specific embodiment, the mini-trap is a dimer. One exemplification of this embodiment of the mini-trap of the invention is a dimer of the fusion protein shown in SEQ ID NO:2, wherein each fusion protein (R1R2-cMC) has a molecular weight of 23.0 kD and a pI of 9.22.

In another embodiment, cMC is 4 amino acids in length consisting of two cysteine residues, for example, XCXC (SEQ ID NO:3). In one exemplification of this embodiment of the invention, the mini-trap consists of the VEGF receptor components of the invention, and a cMC consisting of ACGC (SEQ ID NO:4). One exemplification of this embodiment of the mini-trap of the invention is a dimer of the fusion protein shown in SEQ ID NO:5, wherein each monomer has a molecular weight of 23.2 kD and a pI of 9.22.

In all embodiments of the VEGF trap of the invention (including truncated VEGF mini-trap, VEGF mini-traps, and monomeric VEGF mini-traps), a signal sequence (S) may be included at the beginning (or N-terminus) of the fusion polypeptide of the invention. The signal sequence may be native to the cell, recombinant, or synthetic. When a signal sequence is attached to the N-terminus of a first receptor component, thus a fusion protein may be designated as, for example, $S-(R1R2)_X$.

The invention encompasses vectors comprising the nucleic acid molecules of the invention, including expression vectors comprising a the nucleic acid molecules operatively linked to an expression control sequence. The invention further encompasses host-vector systems for the production of a fusion polypeptide which comprise the expression vector, in a suitable host cell; host-vector systems wherein the suitable host cell is a bacterial, yeast, insect, mammalian cell; an *E. coli* cell, or a COS or CHO cell. Additional encompassed are VEGF traps of the invention modified by acetylation or pegylation. Methods for acetylating or pegylating a protein are well known in the art.

In a related ninth aspect, the invention features a method of producing a VEGF trap of the invention, comprising culturing a host cell transfected with a vector comprising a nucleic acid sequence of the invention, under conditions suitable for expression of the protein from the host cell, and recovering the fusion protein so produced.

The VEGF traps of the invention are therapeutically useful for treating any disease or condition which is improved, ameliorated, or inhibited by removal, inhibition, or reduction of VEGF. A non-exhaustive list of specific conditions improved by inhibition or reduction of VEGF include, for example, undesirable plasma leakage, undesirable blood vessel growth, e.g., such as in a tumor, edema, cancer-associated ascites formation, diabetes, ocular diseases and inflammatory skin diseases such as psoriasis.

Accordingly, in a tenth aspect, the invention features a therapeutic method for the treatment of a VEGF-related disease or condition, comprising administering a VEGF trap of the invention to a subject suffering from a VEGF-related disease or condition. Although any mammal can be treated by the therapeutic methods of the invention, the subject is preferably a human patient suffering from or at risk of suffering from a condition or disease which can be improved, ameliorated, inhibited or treated with a VEGF trap.

In a eleventh aspect, the invention further features diagnostic and prognostic methods, as well as kits for detecting, quantitating, and/or monitoring VEGF with the mini-traps of the invention.

In a twelfth aspect, the invention features pharmaceutical compositions comprising a VEGF trap of the invention with a pharmaceutically acceptable carrier. Such pharmaceutical compositions may comprise a dimeric fusion protein trap, or nucleic acids encoding the fusion polypeptide. The mini-traps of the invention find specific uses in conditions in which a VEGF trap with reduced serum half life (e.g., faster clearance), and/or increased tissue penetration due to smaller size is desirable. Specific applications for the VEGF mini-trap include, for example, diseases where local administration to a specific tissue or cell is desirable. One example of such a condition or disease are ocular diseases of the eye.

Other objects and advantages will become apparent from a review of the ensuing detailed description.

DETAILED DESCRIPTION OF THE INVENTION

Figure 1:
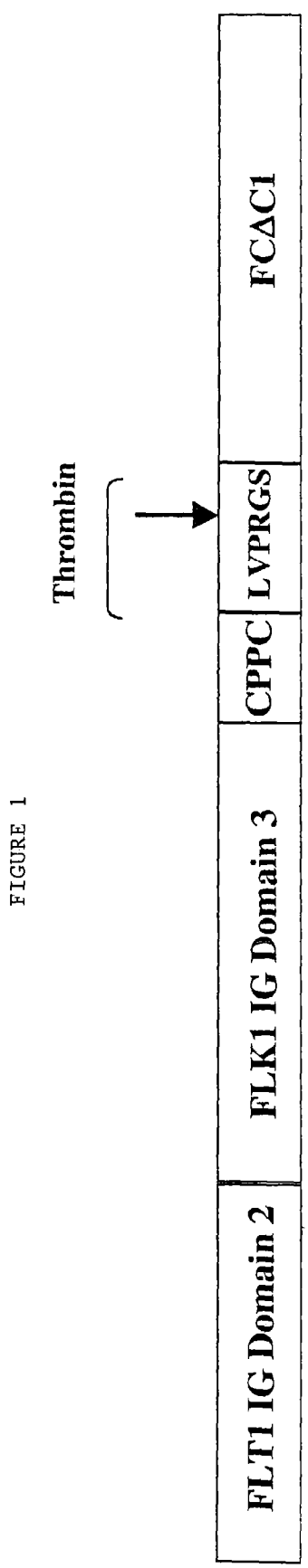
FIG. 1 is a schematic illustration showing insertion of a thrombin cleavage site (LVPRGS) (SEQ ID NO:6) into a full-sized parent VEGF trap (Flt1D2.Flk1.D3.FcΔC1) (SEQ ID NO:10) following the second cysteine residue of the Fc domain.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to describe the methods and/or materials in connection with which the publications are cited.

General Description

The invention encompasses a VEGF trap capable of binding and inhibiting VEGF activity which is a monomer or multimer of one or more fusion polypeptides. The molecules of the invention bind and inhibit the biological action of VEGF and/or the physiological reaction or response. For a description of VEGF-receptor-based antagonist VEGF traps Flt1D2.Flk1D3.FcΔC1(a) (SEQ ID NOs:7–8) and VEGFR1R2-FcΔC1(a) (SEQ ID NOs:9–10), see PCT WO/0075319, the contents of which is incorporated in its entirety herein by reference.

The mini-trap of the invention is smaller than the full sized trap, e.g., about 50–60 kD versus 120 kD of the parent trap, and include monomeric traps consisting essentially of VEGF receptor domains $(R1R2)_X$, $(R1R3)_Y$, or combinations thereof, traps generated by cleavage of a portion of a parent multimerized trap having an MC-containing a cleavage region (C-region); or by attaching a cysteine residue or amino acid sequence containing one or more cysteine residues to or between receptor component domains. In specific embodiments, the mini-trap of the invention is less than about 60 kD as measured by SDS-PAGE analysis; more preferably, about 50 kD; even more preferably about 20–30 kD; or is about 25 kD and capable of binding VEGF with an affinity comparable to a full-sized parent trap described in PCT/US00/14142.

The VEGF mini-traps of the invention are particularly useful in specific applications where a smaller size allows the mini-trap to penetrate to a target tissue. Generally the traps will be dimers formed from two identical fusion proteins comprising, in any order, R1R2 and/or R1R3 (as defined above).

Nucleic Acid Constructs and Expression

The present invention provides for the construction of nucleic acid molecules encoding fusion proteins capable of binding VEGF alone or multimerized VEGF traps. The nucleic acid molecules of the invention may encode wild-type R1, R2, and/or R3 receptor components, or functionally equivalent variants thereof. Amino acid sequence variants of the R1, R2 and/or R3 receptor components of the traps of the invention may also be prepared by creating mutations in the encoding nucleic acid molecules. Such variants include, for example, deletions from, or insertions or substitutions of, amino acid residues within the amino acid sequence of R1, R2 and/or R3. Any combination of deletion, insertion, and substitution may be made to arrive at a final construct, provided that the final construct possesses the ability to bind and inhibit VEGF.

These nucleic acid molecules are inserted into a vector that is able to express the fusion proteins when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the fusion proteins of the invention under control of transcriptional/translational control signals.

Expression of the nucleic acid molecules of the invention may be regulated by a second nucleic acid sequence so that the molecule is expressed in a host transformed with the recombinant DNA molecule. For example, expression may be controlled by any promoter/enhancer element known in the art. Promoters which may be used to control expression of the chimeric polypeptide molecules include, but are not limited to, a long terminal repeat (Squinto et al. (1991) Cell 65:1–20); SV40 early promoter region, CMV, M-MuLV, thymidine kinase promoter, the regulatory sequences of the metallothionine gene; prokaryotic expression vectors such as the b-lactamase promoter, or the tac promoter (see also Scientific American (1980) 242:74–94); promoter elements from yeast or other fungi such as Gal 4 promoter, ADH, PGK, alkaline phosphatase, and tissue-specific transcriptional control regions derived from genes such as elastase I.

Expression vectors capable of being replicated in a bacterial or eukaryotic host comprising the nucleic acid molecules of the invention are used to transfect the host and thereby direct expression of such nucleic acids to produce the fusion proteins of the invention, which form traps capable of binding to VEGF. Transfected cells may transiently or, preferably, constitutively and permanently express the VEGF traps of the invention.

The traps of the invention may be purified by any technique which allows for the subsequent formation of a stable, biologically active trap. For example, and not by way of limitation, the factors may be recovered from cells either as soluble proteins or as inclusion bodies, from which they may be extracted quantitatively by 8M guanidinium hydrochloride and dialysis (see, for example, U.S. Pat. No. 5,663,304). In order to further purify the factors, conventional ion exchange chromatography, hydrophobic interaction chromatography, reverse phase chromatography or gel filtration may be used.

VEGF Receptor Components

The VEGF receptor components of the VEGF mini trap consist of the Ig domain 2 of Flt-1 (Flt1D2) (R1), the Ig domain 3 of Flk-1 (Flk1D3) (R2) (together, R1R2), and/or R1 and Ig domain 3 of Flt-4 (Flt1D3) (R3) (together, R1R3). The term "Ig domain" of Flt-1, Flt-4, or Flk-1 is intended to encompass not only the complete wild-type domain, but also insertional, deletional, and/or substitutional variants thereof which substantially retain the functional characteristics of the intact domain. It will be readily apparent to one of skill in the art that numerous variants of the above Ig domains can be obtained which will retains substantially the same functional characteristics as the wild-type domain.

The term "functional equivalents" when used in reference to R1, R2, or R3, is intended to encompass an R1, R2, or R3 domain with at least one alteration, e.g., a deletion, addition, and/or substitution, which retains substantially the same functional characteristics as does the wild type R1, R2, or R3 domain, that is, a substantially equivalent binding to VEGF. It will be appreciated that various amino acid substitutions can be made in R1, R2, or R3 without departing from the spirit of the invention with respect to the ability of these receptor components to bind and inactivate VEGF. The functional characteristics of the traps of the invention may be determined by any suitable screening assay known to the art for measuring the desired characteristic. Examples of such assays are described in the experimental section below which allow determination of binding characteristics of the traps for VEGF (Kd), as well as their half-life of dissociation of the trap-ligand complex $(T_{1/2})$. Other assays, for example, a change in the ability to specifically bind to VEGF can be measured by a competition-type VEGF binding assay. Modifications of protein properties such as thermal stability, hydrophobicity, susceptibility to proteolytic degradation, or tendency to aggregate may be measured by methods known to those of skill in the art.

Together with the multimerizing component (MC), these components may be arranged in desired order, for example, $(R1R2)_X$-MC; $(R1R2)_X$-MC-$(R1R2)_X$; MC-$(R2R1)_X$, etc. The components of the fusion protein may be connected directly to each other or be connected via spacers. Generally, the term "spacer" (or linker) means one or more molecules, e.g., nucleic acids or amino acids, or non-peptide moieties, such as polyethylene glycol, which may be inserted between one or more component domains. For example, spacer sequences may be used to provide a desirable site of interest between components for ease of manipulation. A spacer may also be provided to enhance expression of the fusion protein from a host cell, to decrease steric hindrance such that the component may assume its optimal tertiary structure and/or interact appropriately with its target molecule. For spacers and methods of identifying desirable spacers, see, for example, George et al. (2003) Protein Engineering 15:871–879, herein specifically incorporated by reference. A spacer sequence may include one or more amino acids naturally connected to a receptor component, or may be an added sequence used to enhance expression of the fusion protein, provide specifically desired sites of interest, allow component domains to form optimal tertiary structures and/or to enhance the interaction of a component with its target molecule. In one embodiment, the spacer comprises one or more peptide sequences between one or more components which is (are) between 1–100 amino acids, preferably 1–25.

In the most specific embodiments, R1 is amino acids 27–126 of SEQ ID NO:8, or 1–126 of SEQ ID NO:8 (including the signal sequence 1–26); or amino acids 27–129 of SEQ ID NO:10, or 1-129 of SEQ ID NO:10 (including the signal sequence at 1–26). In the most specific embodiments, R2 is amino acids 127–228 of SEQ ID NO:8, or amino acids 130–231 of SEQ ID NO:10. In the most specific embodiments, R3 is amino acids 127–225 of SEQ ID NO: 13 (without a signal sequence). When, for example, R2 is placed at the N-terminus of the fusion protein, a signal sequence may desirably precede the receptor component. The receptor component(s) attached to the multimerizing component may further comprise a spacer component, for example, the GPG sequence of amino acids 229–231 of SEQ ID NO:7.

Multimerizing Component

The multimerizing component (MC) is any natural or synthetic sequence capable of interacting with another MC to form a higher order structure, e.g., a dimer, a trimer, etc. Suitable MCs may include a leucine zipper, including leucine zipper domains derived from c-jun or c-fos; sequences derived from the constant regions of kappa or lambda light chains; synthetic sequences such as helix-loop-helix motifs (Muller et al. (1998) FEBS Lett. 432:45–49), coil-coil motifs, etc., or other generally accepted multimerizing domains known to the art.

Generation of Truncated VEGF Mini-Traps

Figure 4:
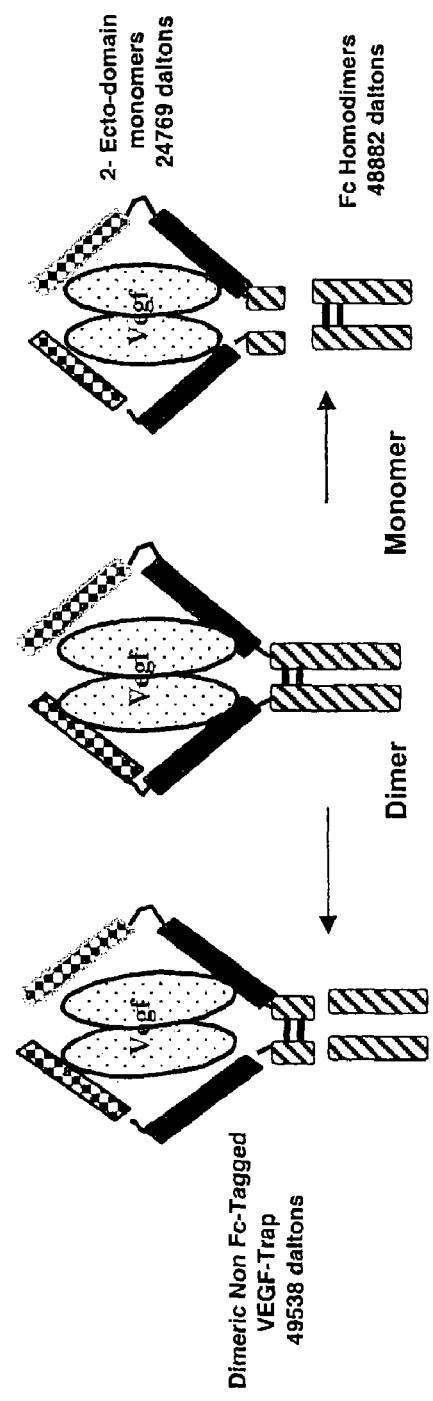
FIG. 4 is a schematic illustration showing truncated dimeric mini-traps formed as a result of MC cleavage of one or both parent fusion polypeptides.

In one embodiment of the trap of the invention, a truncated VEGF mini-trap comprising two or more fusion proteins of the invention, is generated by subjecting a parent trap having C-region-containing MCs to conditions under which one or more of the C-region-containing MCs is (are) cleaved. The resulting truncated mini-trap may be a full and partial cleavage product of a parent trap (see, for example, FIG. 4).

The C-region-containing MC may be any MC capable of interacting with another MC to form a higher order structure, e.g., a dimer or a trimer. The C-region may be created within an MC at any desired location. In light of the guidance provided in the examples below, one of skill in the art would be able to select a desired site for creation of a C-region based on the desired properties of the resulting truncated traps, e.g., molecular weight, monomeric or dimeric, etc.

In a specific embodiment, the C-region is a thrombin cleavage site (LVPRGS) (SEQ ID NO:6) inserted into an FcΔC1 domain following the N-terminal CPPC sequence (SEQ ID NO:1) (FIG. 1). In this embodiment, a full-sized parent VEGF trap construct is expressed in a cell as an Fc-tagged protein, thus allowing capture and purification by, for example, a Protein A column. Following formation of a dimer and covalent bonding between one or both of the cysteine residues of the CPPC sequence (SEQ ID NO:1), the dimer is exposed to thrombin under conditions which cleave one or both of the FcΔC1 domains such that truncated dimeric mini-traps are generated (see FIG. 4), having a molecular weight of approximately 50 kD~90 kD, and has an affinity for VEGF comparable to that of the parent trap. The conditions of cleavage may be controlled by one of skill in the art to favor formation of the partial cleavage product or the fully cleaved product, the choice of cleavage conditions selected by desire for a particular product having specific properties such as molecular weight.

Figure 2:
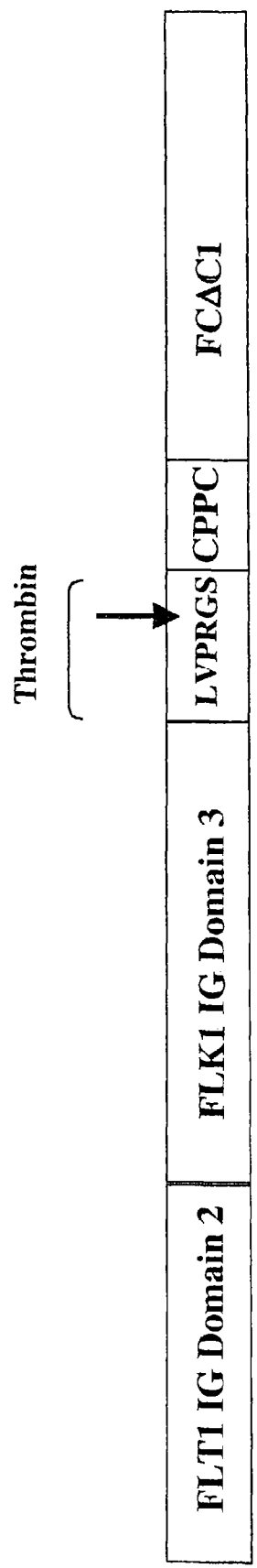
FIG. 2 is a schematic illustration showing insertion of a thrombin cleavage site (LVPRGS) (SEQ ID NO:6) into a full-sized parent VEGF trap (Flt1D2.Flk1.D3.FcΔC1) (SEQ ID NO:10) prior to the first cysteine residue of the Fc domain.

In a specific embodiment, the C-region is a thrombin cleavage site (LVPRGS) (SEQ ID NO:6) inserted into an FcΔC1 domain N-terminal to the CPPC sequence (SEQ ID NO:1) (FIG. 2). Following formation of a dimer and covalent bonding between one or both of the cysteine residues of the CPPC sequence (SEQ ID NO:1), the dimer is exposed to thrombin under conditions in which one or both of the FcΔC1 domain occur and truncated monomeric mini-traps are generated (see FIG. 3). The monomeric truncated mini-trap thus generated comprises a receptor component, and a small fragment of the Fc, and is approximately 25 kD in size and exhibits a reduced affinity for VEGF relative to the truncated dimeric trap and the full length parent trap. A similar monomeric trap produced as a recombinant protein has been shown to have a $K_D$ of about 1 nM.

Generation of VEGF Mini-Traps

In one embodiment, the invention features VEGF mini-traps having one or more receptor component domains $(R1R2)_X$ and/or $(R1R3)_Y$, wherein $X \geq 1$, $Y \geq 1$, and R1, R2, and R3 are as defined above, and optionally, an MC domain which is an amino acid sequence between 1 to about 200 amino acids in length comprising at least one cysteine residue, wherein the at least one cysteine residue is capable of forming a disulfide bond with a cysteine residue present in the MC of another fusion polypeptide (cMC). The cMC may occur at the N-terminus or C-terminus of a fusion protein, or between two receptor component domains. In one specific embodiment, cysteine is added to the C-terminus of a VEGF receptor component, e.g., $R1R2_C$, which allows the fusion polypeptide to form covalent dimers through formation of a covalent disulfide bond between the cysteine residue at the C-terminus of one fusion polypeptide and the cysteine residue at the C-terminus of another fusion polypeptide. In this exemplification, the mini-trap is a dimer of the fusion protein shown in SEQ ID NO:2, wherein each fusion protein (R1R2-cMC or $R1R2_C$) has a molecular weight of about 23.0 kD.

In another embodiment, the cMC is a sequence of 4 amino acids (XXXX) (SEQ ID NO:11) wherein X is any amino acid and the sequence comprises at least one cysteine residue. In a specific embodiment, the cMC is added to the C-terminus of a receptor component domain. In a more specific embodiment, the 4 amino acid sequence is ACGC (SEQ ID NO:4) and the cMC forms two disulfide bonds with the cysteine residues present in a second fusion protein. As shown below in Table 2, both the exemplified mini-traps exhibit an affinity for VEGF comparable to the parent trap.

Therapeutic Uses

The VEGF mini-traps of the invention are therapeutically useful for treating any disease or condition which is improved, ameliorated, inhibited or prevented by removal, inhibition, or reduction of VEGF. A non-exhaustive list of specific conditions improved by inhibition or reduction of VEGF include, clinical conditions that are characterized by excessive vascular endothelial cell proliferation, vascular permeability, edema or inflammation such as brain edema associated with injury, stroke or tumor; edema associated with inflammatory disorders such as psoriasis or arthritis, including rheumatoid arthritis; asthma; generalized edema associated with burns; ascites and pleural effusion associated with tumors, inflammation or trauma; chronic airway inflammation; capillary leak syndrome; sepsis; kidney disease associated with increased leakage of protein; and eye disorders such as age related macular degeneration and diabetic retinopathy.

A smaller, non-glycosylated mini-trap expressed in *E. coli* (Example 4), a glycosylated mini-trap expressed in CHO cells (Example 5), or a receptor-based monomeric trap (Example 6) has optimized characteristics for local/intravitreal delivery, ie. a shorter serum half life for faster clearance and minimizing unwanted systemic exposure. In addition due to its smaller size, the mini-trap has the ability to penetrate through the inner-limiting membrane (ILM) in the eye, and diffuse through the vitreous to the retina/retinal pigment epithelial (RPE) layer which will help to treat retinal disease. Additionally, the mini-trap can be used for local administration for the treatment of ocular disease such as choroidal neovascularization, diabetic macular edema, proliferative diabetic retinopathy, corneal neovascularization/transplant rejection. Still further, the mini-trap can be used in any situation where transient (short-term) blocking of VEGF is required, e.g., to avoid chronic exposure to VEGF blockade, such as, for example, in the treatment of psoriasis.

Combination Therapies

In numerous embodiments, the mini-traps may be administered in combination with one or more additional compounds or therapies. For example, multiple mini-traps can be co-administered, or one or more mini-traps can be administered in conjunction with one or more therapeuatic compounds. When a trap of the invention removes VEGF, the one or more other therapeutic agent is one that is used to prevent or treat a condition associated with the presence of VEGF. A benefit of the combined use of the mini-trap of the invention with a second therapeutic agent is that it provides improved efficacy and/or reduced toxicity of the second therapeutic agent.

Methods of Administration

The invention provides methods of treatment comprising administering to a subject an effective amount of a VEGF mini-trap of the invention. In a preferred aspect, the mini-trap is substantially purified (e.g., substantially free from substances that limit its effect or produce undesired side-effects). The subject is preferably a mammal, and most preferably a human.

Various delivery systems are known and can be used to administer an agent of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429–4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, intraocular, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Administration can be acute or chronic (e.g. daily, weekly, monthly, etc.) or in combination with other agents. Pulmonary administration can also be employed, e.g., by use of an inhaler or nebulizer, and formulation with an aerosolizing agent.

In another embodiment, the active agent can be delivered in a vesicle, in particular a liposome, in a controlled release system, or in a pump. In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), by direct injection, or by use of microparticle bombardment, or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864–1868), etc. Alternatively, a nucleic acid can be introduced intracellularly and incorporated within host cell DNA for expression, by homologous recombination.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes.

A composition useful in practicing the methods of the invention may be a liquid comprising an agent of the invention in solution, in suspension, or both. The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment. Further, the composition can take the form of a solid article that can be inserted in the eye, such as for example between the eye and eyelid or in the conjunctival sac, where the VEGF trap is released. Release from such an article is usually to the cornea, either via the lacrimal fluid, or directly to the cornea itself, with which the solid article is generally in direct contact. Solid articles suitable for implantation in the eye are generally composed primarily of bioerodible or nonbioerodible polymers. An aqueous solution and/or suspension can be in the form of eye drops. A desired dosage of the active agent can be measured by administration of a known number of drops into the eye. For example, for a drop volume of 25 µl, administration of 1–6 drops will deliver 25–150 µl of the composition.

An aqueous suspension or solution/suspension useful for practicing the methods of the invention may contain one or more polymers as suspending agents. Useful polymers include water-soluble polymers such as cellulosic polymers and water-insoluble polymers such as cross-linked carboxyl-containing polymers. An aqueous suspension or solution/suspension of the present invention is preferably viscous or muco-adhesive, or even more preferably, both viscous or mucoadhesive.

In another embodiment, the composition useful in practicing the methods of the invention is an in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein is includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye.

Diagnostic and Screening Methods

The VEGF mini-traps of the invention may be used diagnostically and/or in screening methods. For example, the trap may be used to monitor levels of VEGF during a clinical study to evaluate treatment efficacy. In another embodiment, the methods and compositions of the present invention are used to screen individuals for entry into a clinical study to identify individuals having, for example, too high or too low a level of VEGF. The traps can be used in methods known in the art relating to the localization and activity of VEGF, e.g., imaging, measuring levels thereof in appropriate physiological samples, in diagnostic methods, etc.

The traps of the invention may be used in in vivo and in vitro screening assay to quantify the amount of non-bound VEGF present, e.g., for example, in a screening method to identify test agents able to decrease the expression of VEGF. More genenerally, the traps of the invention may be used in any assay or process in which quantification and/or isolation of VEGF is desired.

Pharmaceutical Compositions

The present invention also provides pharmaceutical compositions comprising a VEGF mini-trap of the invention. Such compositions comprise a therapeutically effective amount of one or more mini-traps, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin.

The VEGF mini-trap of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Further more, aqueous compositions useful for practicing the methods of the invention have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers are included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The amount of the trap that will be effective for its intended therapeutic use can be determined by standard clinical techniques based on the present description. In addition, in vitro assays may optionally be employed to help identify optimal dosage ranges. Generally, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds that are sufficient to maintain therapeutic effect. In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration, and the judgment of the prescribing physician. The therapy may be repeated intermittently while symptoms are detectable or even when they are not detectable. The therapy may be provided alone or in combination with other drugs.

Cellular Transfection and Gene Therapy

The present invention encompasses the use of nucleic acids encoding the fusion polypeptides and mini-traps of the invention for transfection of cells in vitro and in vivo. These nucleic acids can be inserted into any of a number of well-known vectors for transfection of target cells and organisms. The nucleic acids are transfected into cells ex vivo and in vivo, through the interaction of the vector and the target cell. The compositions are administered (e.g., by injection into a muscle) to a subject in an amount sufficient to elicit a therapeutic response. An amount adequate to accomplish this is defined as "a therapeutically effective dose or amount."

In another aspect, the invention provides a method of reducing VEGF levels in a human or other animal comprising transfecting a cell with a nucleic acid encoding a fusion polypeptide of the invention, wherein the nucleic acid comprises an inducible promoter operably linked to the nucleic acid encoding the fusion polypeptide or mini-trap. For gene therapy procedures in the treatment or prevention of human disease, see for example, Van Brunt (1998) Biotechnology 6:1149–1154.

Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Transgenic Animals

The invention includes transgenic non-human animals expressing a mini-trap of the invention. A transgenic animal can be produced by introducing nucleic acid into the male pronuclei of a fertilized oocyte, e.g., by microinjection, retroviral infection, and allowing the oocyte to develop in a pseudopregnant female foster animal. Any of the regulatory or other sequences useful in expression vectors can form part of the transgenic sequence. A tissue-specific regulatory sequence(s) can be operably linked to the transgene to direct expression of the transgene to particular cells. A transgenic non-human animal expressing a fusion polypeptide or mini-trap of the invention is useful in a variety of applications, including as a means of producing such a fusion proteins Further, the transgene may be placed under the control of an inducible promoter such that expression of the fusion polypeptide or mini-trap may be controlled by, for example, administration of a small molecule.

Specific Embodiments

In the experiments described below, smaller VEGF traps were generated and their ability to bind VEGF was investigated. Such mini-traps are preferably uses in specific applications. For example, certain conditions or diseases may be preferably treated with local administration of a VEGF trap to a specific organ, tissue, or cell, rather than by systemic administration. In one exemplification of the mini-traps of the invention, a smaller VEGF trap was generated by directed cleavage of a dimerized VEGF trap having a cleavage region (C-region) generated in a Fc domain (Example 2). The truncated trap exhibited comparable affinity for VEGF and half-life as the full-sized parent trap. Examples 3–5 describe construction of fusion proteins having a VEGF receptor component and a multimerizing component consisting of one or two cysteine residues. Affinity measurements showed that the non-glycosylated fusion polypeptides expressed in *E. coli* or the glycosylated polypeptides expressed in CHO cells had comparable binding affinity for VEGF as the full-sized parent trap. Example 6 further illustrates a monomeric VEGF trap consisting of $(R1R2)_2$ which is capable of binding and inhibiting VEGF.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Construction of Flt1D2.Flk1D3.FcΔC1(a)

The construction of a parent VEGF trap, Flt1D2.Flk1D3.FcΔC1(a) (SEQ ID NOs:7–8), VEGFR1R2.FcΔC1(a) (SEQ ID NOs:9–10), and Flt1D2.VEGFR3D3.FcΔC1(a) (SEQ ID NOs: 12–13) is described in detail in PCT publication WO/0075319, herein specifically incorporated by reference in its entirety. Also described in WO/0075319 are methods of constructing and expressing nucleic acid constructs encoding VEGF traps, methods of detecting and measuring VEGF trap binding to VEGF, methods of determining the stoichiometry of VEGF binding by BIAcore analysis, and pharmacokinetic analyses.

Example 2

Thrombin-Cleaved Dimeric VEGF Mini-Trap

Figure 3:
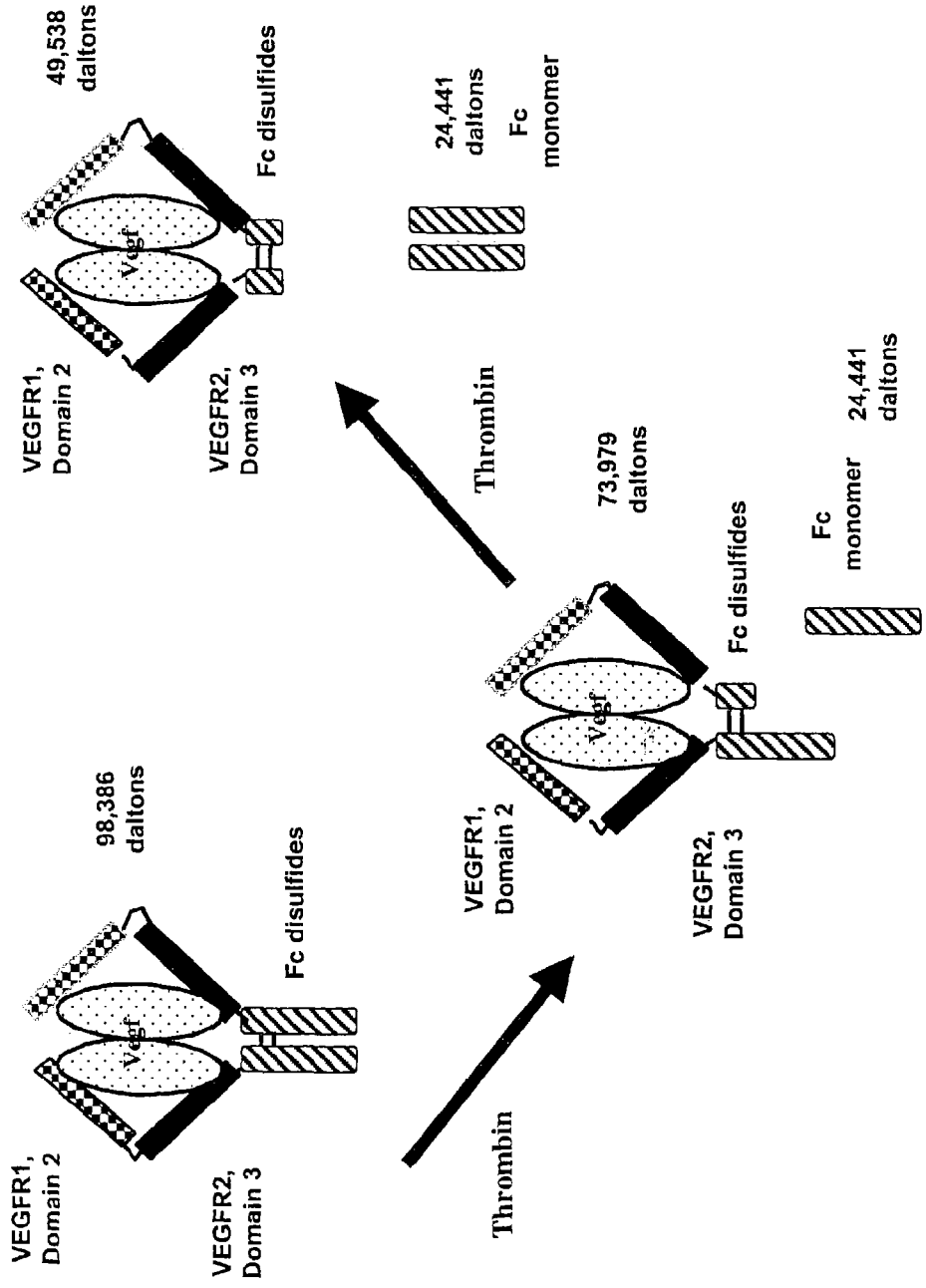
FIG. 3 is a schematic illustration of dimeric or monomeric VEGF mini-traps generated via cleavage of the Fc domain.

The VEGFR1R2.FcΔC1(a) (SEQ ID NOs:9–10) construct was modified by insertion of a thrombin cleavage following the CPPC (SEQ ID NO:1) of the Fc domain (FIG. 3). Purified VEGF trap (5 μg) was incubated with thrombin (Novagen) in 20 mM Tris-HCl, pH 8.4, 50 mM NaCl, 2.5 mM $CaCl_2$ for 16 hrs at 37° C. Controls included cleavage control protein (CCP) and parent VEGF trap protein incubated without thrombin. SDS-PAGE analysis (Tris-Glycine 4–20% gel; 5 μg protein per lane) verified correct cleavage (results not shown).

Affinity determination. The Kd of binding of each VEGF trap to hVEGF165 was determined as described in WO/0075319, for the parent VEGF trap, uncleaved VEGF trap containing a thrombin cleavage site ("uncleaved VEGF trap"), cleaved VEGF mini-trap and recombinant monomeric R1R2-myc myc his. More specifically, the ability of the traps to block $VEGF_{165}$-dependent receptor phosphorylation was determined using primary human endothelial cells (HUVECs). $VEGF_{165}$ was incubated in the presence of varying concentrations of the test traps, and the mixture was added to HUVECs to stimulate tyrosine phosphorylation of VEGFR2. At sub-stoichiometric concentrations of VEGF trap, unbound VEGF induced receptor phosphorylation. However, at a 1:1 molar ratio of greater of a VEGF trap to ligand, complete blocking of receptor signaling was observed, establishing that a single molecule of a trap dimer is capable of blocking a single molecule of human $VEGF_{165}$. Thus, the high binding affinity of the VEGF trap for VEGF results in formation of a complex that prevents VEGF from interaction with cell surface receptors. Equivalent results were obtained for identical phosphorylation inhibition experiments for the parent VEGF trap, uncleaved VEGF trap, and cleaved VEGF mini-trap The results are shown in Table 1.

TABLE 1

| Trap | Kinetic Dissociation Rate (1/s) | $T_{1/2}$ (hr) |
|---|---|---|
| parent VEGF trap | $5.51 \times 10^{-5}$ ± 0.94% | 3.5 |
| uncleaved VEGF trap | $4.93 \times 10^{-5}$ ± 0.70% | 3.9 |
| cleaved VEGF mini-trap | $5.46 \times 10^{-5}$ ± 0.62% | 3.53 |
| R1R2-myc myc his monomer | $6.74 \times 10^{-3}$ ± 0.38% | 0.028 |

Example 3

Construction of Plasmids Encoding VEGF Mini-Traps

VEGF mini-traps were constructed from a precursor of the parent VEGF trap, VEGFR1R2.FcΔC1(a) (SEQ ID NOs:9–10), in which the three amino acids glycine-alanine-proline served as a linker between the Flk1 D3 and FcΔC1(a). This plasmid, pTE115 was used in the construction of the VEGF mini-traps because the linker DNA sequence included a SrfI restriction endonuclease recognition sequence that facilitated engineering the VEGF trap. In all other respects, the VEGF trap encoded by pTE115 is identical to that of the VEGF trap, VEGFR1R2.FcΔC1(a) (SEQ ID NOs:9–10) described in detail in PCT publication WO/0075319.

Two VEGF mini-traps were constructed with multimerization domains consisting of either a single cysteine residue ($R1R2_C$) (SEQ ID NO:2) or the amino acids ACGC (SEQ ID NO:4) ($R1R2_{ACGC}$) (SEQ ID NO:5) added to the C-terminus of receptor components Flt1D2.Flk1D3. Both of these constructs are capable of forming homo-dimeric molecules stabilized by one ($R1R2_C$) or two ($R1R2_{ACGC}$) intermolecular disulfides.

The plasmid pTE517 was made by removing the 690 bp fragment generated by digestion of pTE115 DNA with SrfI and NotI and inserting the synthetic DNA fragment formed by annealing the oligos R1R2NC (SEQ ID NO:14) and R1R2CC (SEQ ID NO:15). The resulting plasmid encodes $R1R2_C$, which consists of the Flt1D2.Flk1D3 domains followed by a cysteine residue (SEQ ID NO:23). Similarly, the plasmid pTE518 was made by removing the 690 bp fragment generated by digestion of pTE115 DNA with SrfI and NotI, followed by ligation with the synthetic DNA fragment formed by annealing the oligos R1R2NACGC (SEQ ID NO:18) and R1R2CACGC (SEQ ID NO:19). The resulting plasmid encodes $R1R2_{ACGC}$, which consists of the Flt1D2.Flk1D3 domains followed by the amino acids ACGC (SEQ ID NO:25).

Plasmids were also constructed to direct the expression of these mini-traps in *E. coli*. The primers R1R2N-Nco1 (SEQ ID NO:16) and R1R2CNot1 (SEQ ID NO:17) were used to amplify a DNA fragment from pTE115 that encodes amino acids G30 to K231, relative to the parental VEGF trap (SEQ ID NO:10). Amplification of this sequence resulted in fusion of an initiating methionine codon at the 5' end and fusion of the codon for cysteine, followed by a stop codon, at the 3' end (SEQ ID NO:2). This DNA fragment was then cloned into the Nco I and Not I sites of the *E. coli* expression plasmid pRG663 to yield pRG1102 such that expression of $R1R2_C$ was dependent on transcription from the phage T7 Φ1.1 promoter. Induction of gene expression from pRG 1102 results in accumulation of R1R2cys in the cytoplasm of the *E. coli* host strain RFJ238. Similarly, the primers R1R2N-Nco1 (SEQ ID NO:16) and R1R2ACGC-Not1 (SEQ ID NO:20) were used to amplify a DNA fragment from pTE115 that encodes amino acids G30 to K231 (SEQ ID NO:10) resulting in fusion of an initiating methionine codon at the 5' end and fusion of codons for ACGC (SEQ ID NO:4), followed by a stop codon, at the 3' end (SEQ ID NO:5). This fragment was then cloned into the Nco I and NotI sites of the *E. coli* expression plasmid pRG663 to yield pRG1103 such that expression of $R1R2_{ACGC}$ was dependent on transcription from the phage T7 Φ1.1 promoter. Induction of gene expression from both pRG1102 and pRG1103 resulted in accumulation of $R1R2_C$ or $R1R2_{ACGC}$, respectively, in the cytoplasm of the *E. coli* host strain RFJ238.

Example 4

Purification and Characterization of VEGF Mini-Traps From *E. coli*

Both $R1R2_C$ and $R1R2_{ACGC}$ were expressed as cytoplasmic proteins in *E. coli* and were purified by the same method. Induction of the phage T7 Φ1.1 promoter on either pRG1102 or pRG1103 in the *E. coli* K12 strain RFJ238 resulted in accumulation of the protein in the cytoplasm. After induction, cells were collected by centrifugation, resuspended in 50 mM Tris-HCl, pH 7.5, 20 mM EDTA, and lysed by passage through a Niro-Soavi cell homogenizer. Inclusion bodies were collected from lysed cells by centrifugation, washed once in distilled $H_2O$, then solubilized in 8 M guanidinium-HCl, 50 mM Tris-HCl, pH 8.5, 100 mM sodium sulfite, 10 mM sodium tetrathionate and incubated at room temperature for 16 hours. Clarified supernatant was fractionated on an S300 column equilibrated with 6 M guanidinium-HCl, 50 mM Tris-HCl, pH 7.5. Fractions containing $R1R2_C$ were pooled and dialyzed against 6M Urea, 50 mM Tris-HCl, pH 7.5. Dialyzed protein was diluted to 2M Urea, 50 mM Tris-HCl, pH 8.5, 2 mM cysteine then stirred slowly for 7 days at 4° C. Refolded protein was dialyzed against 50 mM Tris-HCl, pH 7.5 then loaded onto an SP-sepharose column equilibrated with 50 mM Tris-HCl, pH 7.5 and eluted with a NaCl gradient from 0 to 1 M in 50 mM Tris-HCl, pH 7.5. Fractions containing $R1R2_C$ were pooled, concentrated, and loaded onto a Superdex 200 column equilibrated with 50 mM Tris-HCl, pH 7.5, 150 mM NaCl. Fractions containing mini-trap dimer were collected and pooled. The molecular weight of purified mini-trap was estimated to be about 46 kD by SDS-PAGE.

BIAcore assays were conducted (as described in WO/0075319) to determine trap affinity for VEGF, and the results showed that the $R1R2_C$ and $R1R2_{ACGC}$ mini-traps had VEGF affinity comparable to the full length VEGF trap (Table 2).

TABLE 2

| Trap | Kinetic Dissociation Rate (1/s) | $T_{1/2}$ (hr) |
|---|---|---|
| VEGF trap | $4.23 \times 10^{-5}$ | 4.53 |
| $R1R2_C$ | $3.39 \times 10^{-5}$ | 5.68 |
| $R1R2_{ACGC}$ | $3.41 \times 10^{-5}$ | 5.65 |

Example 5

Expression of VEGF Mini-Traps in CHO K1

Figure 5A:
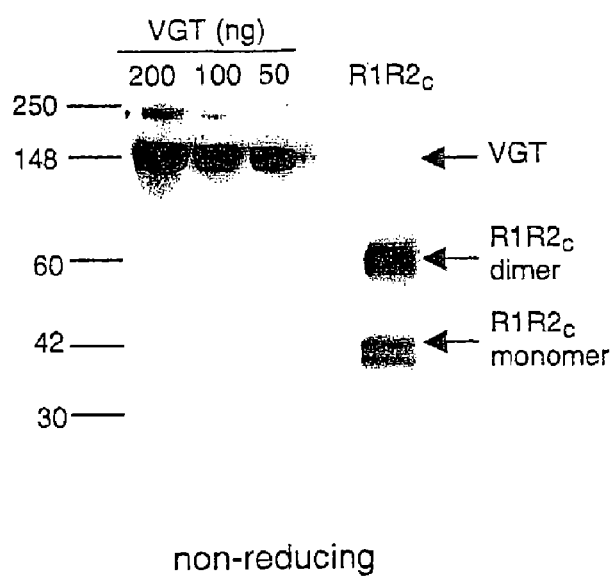
FIGS. 5A–B is a SDS-PAGE analysis under non-reducing (A) or reducing (B) conditions showing efficient covalent dimer formation of $R1R2_C$ when expressed as a secreted protein in CHO cells.
Figure 5B:
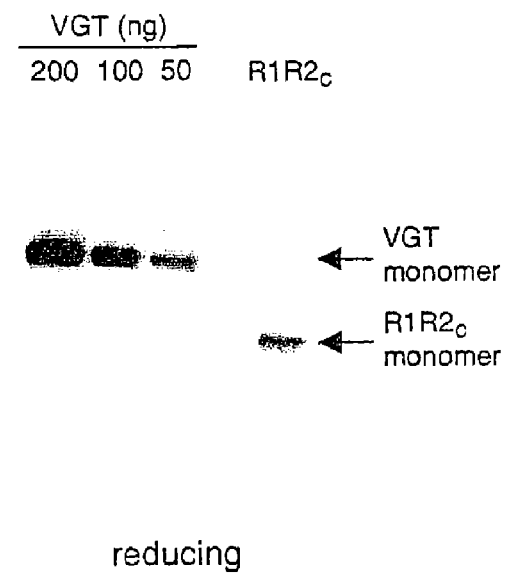

Expression of the VEGF mini-traps encoded by pTE517 and pTE518 is dependent on transcription from the human CMV-MIE promoter and results in secretion of the mini-traps into the culture medium when expressed in CHO cells. When expressed as secreted proteins in CHO K1, both mini-traps were found in the conditioned media and estimation of their molecular weight by SDS-PAGE suggested, as expected, that the proteins were glycosylated. Analysis by SDS-PAGE also indicated that the mini-traps were capable of forming homo-dimeric molecules stabilized by intermolecular disulfide(s) between the C-terminal cysteine(s). Specifically, the R1R2$_C$ mini-trap efficiently formed covalent dimers when expressed as a secreted protein in CHO (FIG. 5A non-reducing; FIG. 5B reducing).

Example 6

Construction and Expression of a Single Chain VEGF Mini-Trap

A VEGF mini-trap was also constructed that did not require a multimerization domain (SEQ ID NO:24). This mini-trap was constructed by direct fusion of one Flt1D2.Flk1D3 domain (R1R2) (amino acids 30–231 of SEQ ID NO:24) to a second Flt1D2.Flk1D3 domain (R1R2) (amino acids 234–435 of SEQ ID NO:24) with a Gly-Pro linker between the tandem receptor domains (amino acids 232–233 of SEQ ID NO:24).

To construct a gene encoding tandem Flt1D2.Flk1D3 domains, a DNA fragment was synthesized (Blue Heron Biotechnology) that encoded one Flt1D2.Flk1D3 domain that minimized DNA homology with the Flt1D2.Flk1D3 domain-encoding DNA found in pTE115. This synthetic DNA fragment was cloned as a Srf I-Not I fragment into the Srf I-Not I sites of pTE115 to yield pTE570, which expresses the R1R2—R1R2 VEGF mini-trap from the CMV-MIE promoter. When this plasmid is transfected into CHO K1 cells the R1R2—R1R2 VEGF mini-trap accumulates in the culture medium.

We claim:

1. An isolated nucleic acid molecule encoding a fusion polypeptide capable of binding vascular endothelial growth factor (VEGF) consisting of components (R1R2)$_X$, and a multimerizing component (MC) capable of interacting with another MC to form a multimeric structure, wherein X≧1, R1 is VEGF receptor component Ig domain 2 of Flt-1 consisting of amino acids 27–126 of SEQ ID NO: 8 or 27–129 of SEQ ID NO: 10, R2 is Ig domain 3 of Flk-1 consisting of amino acids 127–228 of SEQ ID NO: 8 or 130–231 of SEQ ID NO: 10, and MC is an amino acid sequence between 1 to about 200 amino acids in length having at least one cysteine residue.

2. The nucleic acid molecule of claim 1, encoding an amino acid sequence selected from the group consisting of SEQ ID NO: 2, 5, 23 and 25.

3. A replicable expression vector comprising a nucleic acid molecule encoding a fusion protein which binds vascular endothelial growth factor (VEGF), wherein the fusion protein consists of a first receptor component, a second receptor component, and a multimerizing component, wherein the first receptor component is amino acids 27–126 of SEQ ID NO:8 or 27–129 of SEQ ID NO:10, the second receptor component is amino acids 127–228 of SEQ ID NO:8 or 130–231 of SEQ ID NO:10, and the multimerizing component is an amino acid sequence between 1 to about 200 amino acids having at least one cysteine residue.

4. A method of producing a VEGF fusion protein comprising the step of introducing the expression vector of claim 3 into an isolated host cell, growing the cell under conditions permitting production of the fusion protein and recovering the fusion protein so produced.

5. An isolated nucleic acid molecule encoding a fusion polypeptide which binds vascular endothelial growth factor (VEGF), consisting of a first receptor component, a second receptor component, and a multimerizing component, wherein the first receptor component is amino acids 27–126 of SEQ ID NO:8 or 27–129 of SEQ ID NO:10, the second receptor component is amino acids 127–228 of SEQ ID NO:8 or 130–231 of SEQ ID NO:10, and the multimerizing component is an amino acid sequence between 1 to about 200 amino acids having at least one cysteine residue.

6. The isolated nucleic acid molecule of claim 5, wherein the fusion polypeptide is selected from the group consisting of SEQ ID NO:2, 5, 23 and 25.

7. A fusion polypeptide encoded by the nucleic acid molecule of claim 5.

8. The fusion polypeptide of claim 7, wherein the components are connected directly to each other or via one or more spacer sequences.

9. A vascular endothelial cell growth factor (VEGF) trap, comprising a multimer of two or more fusion polypeptides of claim 7.

10. The VEGF trap of claim 9 which is a dimer.

11. The VEGF trap of claim 10, wherein the MC is a cysteine residue and the cysteine residue of a first fusion polypeptide forms a covalent disulfide bond with the cysteine residue of a second fusion polypeptide.

12. A composition comprising the VEGF trap of claim 11 and a pharmaceutically acceptable carrier.

13. The VEGF trap of claim 10, wherein the MC is four amino acids and comprises at least one cysteine residue.

14. A vascular endothelial growth factor (VEGF) trap, comprising a dimer which binds VEGF consisting of two fusion polypeptides, each fusion polypeptide consisting of a first receptor component, a second receptor component, and a multimerizing component (MC), wherein the first receptor component is amino acids 27–126 of SEQ ID NO:8 or 27–129 of SEQ ID NO:10, the second receptor component is amino acids 127–228 of SEQ ID NO:8 or 130–231 of SEQ ID NO:10, and wherein the MC is XCXC (SEQ ID NO:3).

15. A vascular endothelial growth factor (VEGF) trap, comprising a dimer which binds VEGF consisting of two fusion polypeptides, each fusion polypeptide consisting of a first receptor component, a second receptor component, and a multimerizing component (MC), wherein the first receptor component is amino acids 27–126 of SEQ ID NO:8 or 27–129 of SEQ ID NO:10, the second receptor component is amino acids 127–228 of SEQ ID NO:8 or 130–231 of SEQ ID NO:10, and wherein the MC is ACGC (SEQ ID NO:4).

16. A composition comprising the VEGF trap of claim 15 and a pharmaceutically acceptable carrier.

* * * * *

SEQUENCE LISTING

```
<160> NUMBER OF SEQ ID NOS: 25

<210> SEQ ID NO 1
<211> LENGTH: 4
<212> TYPE: PRT
<213> ORGANISM: homo sapiens

<400> SEQUENCE: 1

Cys Pro Pro Cys
 1

<210> SEQ ID NO 2
<211> LENGTH: 200
<212> TYPE: PRT
<213> ORGANISM: homo sapiens

<400> SEQUENCE: 2

Met Gly Arg Pro Phe Val Glu Met Tyr Ser Glu Ile Pro Glu Ile Ile
 1               5                  10                  15

His Met Thr Glu Gly Arg Glu Leu Val Ile Pro Cys Arg Val Thr Ser
                20                  25                  30

Pro Asn Ile Thr Val Thr Leu Lys Lys Phe Pro Leu Asp Thr Leu Ile
            35                  40                  45

Pro Asp Gly Lys Arg Ile Ile Trp Asp Ser Arg Lys Gly Phe Ile Ile
        50                  55                  60

Ser Asn Ala Thr Tyr Lys Glu Ile Gly Leu Leu Thr Cys Glu Ala Thr
65                  70                  75                  80

Val Asn Gly His Leu Tyr Lys Thr Asn Tyr Leu Thr Gln Thr Asn Thr
                85                  90                  95

Ile Ile Asp Val Val Leu Ser Pro Ser His Gly Ile Glu Leu Ser Val
            100                 105                 110

Gly Glu Lys Leu Val Leu Asn Cys Thr Ala Arg Thr Glu Leu Asn Val
        115                 120                 125

Gly Ile Asp Phe Asn Trp Glu Tyr Pro Ser Ser Lys His Gln His Lys
    130                 135                 140

Lys Leu Val Asn Arg Asp Leu Lys Thr Gln Ser Gly Ser Glu Met Lys
145                 150                 155                 160
```

```
Lys Phe Leu Ser Thr Leu Thr Ile Asp Gly Val Thr Arg Ser Asp Gln
                165                 170                 175

Gly Thr Cys Ala Ala Ser Ser Gly Leu Met Thr Lys Lys Asn Ser Thr
            180                 185                 190

Phe Val Arg Val His Glu Lys Cys
        195                 200

<210> SEQ ID NO 3
<211> LENGTH: 4
<212> TYPE: PRT
<213> ORGANISM: homo sapiens
<220> FEATURE:
<221> NAME/KEY: VARIANT
<222> LOCATION: 1, 3
<223> OTHER INFORMATION: Xaa = Any Amino Acid

<400> SEQUENCE: 3

Xaa Cys Xaa Cys
 1

<210> SEQ ID NO 4
<211> LENGTH: 4
<212> TYPE: PRT
<213> ORGANISM: homo sapiens

<400> SEQUENCE: 4

Ala Cys Gly Cys
 1

<210> SEQ ID NO 5
<211> LENGTH: 203
<212> TYPE: PRT
<213> ORGANISM: homo sapiens

<400> SEQUENCE: 5

Met Gly Arg Pro Phe Val Glu Met Tyr Ser Glu Ile Pro Glu Ile Ile
 1               5                  10                  15

His Met Thr Glu Gly Arg Glu Leu Val Ile Pro Cys Arg Val Thr Ser
                20                  25                  30

Pro Asn Ile Thr Val Thr Leu Lys Lys Phe Pro Leu Asp Thr Leu Ile
            35                  40                  45

Pro Asp Gly Lys Arg Ile Ile Trp Asp Ser Arg Lys Gly Phe Ile Ile
        50                  55                  60

Ser Asn Ala Thr Tyr Lys Glu Ile Gly Leu Leu Thr Cys Glu Ala Thr
65                  70                  75                  80

Val Asn Gly His Leu Tyr Lys Thr Asn Tyr Leu Thr Gln Thr Asn Thr
                85                  90                  95

Ile Ile Asp Val Val Leu Ser Pro Ser His Gly Ile Glu Leu Ser Val
                100                 105                 110

Gly Glu Lys Leu Val Leu Asn Cys Thr Ala Arg Thr Glu Leu Asn Val
            115                 120                 125

Gly Ile Asp Phe Asn Trp Glu Tyr Pro Ser Ser Lys His Gln His Lys
        130                 135                 140

Lys Leu Val Asn Arg Asp Leu Lys Thr Gln Ser Gly Ser Glu Met Lys
145                 150                 155                 160

Lys Phe Leu Ser Thr Leu Thr Ile Asp Gly Val Thr Arg Ser Asp Gln
                165                 170                 175

Gly Thr Cys Ala Ala Ser Ser Gly Leu Met Thr Lys Lys Asn Ser Thr
            180                 185                 190
```

```
Phe Val Arg Val His Glu Lys Ala Cys Gly Cys
        195                 200
```

<210> SEQ ID NO 6
<211> LENGTH: 6
<212> TYPE: PRT
<213> ORGANISM: homo sapiens

<400> SEQUENCE: 6

```
Leu Val Pro Arg Gly Ser
 1               5
```

<210> SEQ ID NO 7
<211> LENGTH: 1453
<212> TYPE: DNA
<213> ORGANISM: homo sapiens

<400> SEQUENCE: 7

| | | | | |
|---|---|---|---|---|
| aagcttgggc | tgcaggtcga | tcgactctag | aggatcgatc | cccgggcgag ctcgaattcg | 60 |
| caaccaccat | ggtcagctac | tgggacaccg | ggtcctgct | gtgcgcgctg ctcagctgtc | 120 |
| tgcttctcac | aggatctagt | tccggaggta | gacctttcgt | agagatgtac agtgaaatcc | 180 |
| ccgaaattat | acacatgact | gaaggaaggg | agctcgtcat | tccctgccgg gttacgtcac | 240 |
| ctaacatcac | tgttactta | aaaaagtttc | cacttgacac | tttgatccct gatgaaaac | 300 |
| gcataatctg | ggacagtaga | aagggcttca | tcatatcaaa | tgcaacgtac aaagaaatag | 360 |
| ggcttctgac | ctgtgaagca | acagtcaatg | ggcatttgta | taagacaaac tatctcacac | 420 |
| atcgacaaac | caatacaatc | atagatgtgg | ttctgagtcc | gtctcatgga attgaactat | 480 |
| ctgttggaga | aaagcttgtc | ttaaattgta | cagcaagaac | tgaactaaat gtggggattg | 540 |
| acttcaactg | ggaatacct | tcttcgaagc | atcagcataa | gaaacttgta aaccgagacc | 600 |
| taaaaacca | gtctgggagt | gagatgaaga | aatttttgag | caccttaact atagatggtg | 660 |
| taacccggag | tgaccaagga | ttgtacacct | gtgcagcatc | cagtgggctg atgaccaaga | 720 |
| agaacagcac | atttgtcagg | gtccatgaaa | agggcccggg | cgacaaaact cacacatgcc | 780 |
| caccgtgccc | agcacctgaa | ctcctggggg | gaccgtcagt | cttcctcttc cccccaaaac | 840 |
| ccaaggacac | cctcatgatc | tcccggaccc | ctgaggtcac | atgcgtggtg gtggacgtga | 900 |
| gccacgaaga | ccctgaggtc | aagttcaact | ggtacgtgga | cggcgtggag gtgcataatg | 960 |
| ccaagacaaa | gccgcgggag | gagcagtaca | acagcacgta | ccgtgtggtc agcgtcctca | 1020 |
| ccgtcctgca | ccaggactgg | ctgaatggca | aggagtacaa | gtgcaaggtc tccaacaaag | 1080 |
| ccctcccagc | ccccatcgag | aaaaccatct | ccaaagccaa | agggcagccc cgagaaccac | 1140 |
| aggtgtacac | cctgccccca | tcccgggatg | agctgaccaa | gaaccaggtc agcctgacct | 1200 |
| gcctggtcaa | aggcttctat | cccagcgaca | tcgccgtgga | gtgggagagc aatgggcagc | 1260 |
| cggagaacaa | ctacaagacc | acgcctcccg | tgctggactc | cgacggctcc ttcttcctct | 1320 |
| atagcaagct | caccgtggac | aagagcaggt | ggcagcaggg | gaacgtcttc tcatgctccg | 1380 |
| tgatgcatga | ggctctgcac | aaccactaca | cgcagaagag | cctctccctg tctccgggta | 1440 |
| aatgagcggc | cgc | | | | 1453 |

<210> SEQ ID NO 8
<211> LENGTH: 458
<212> TYPE: PRT
<213> ORGANISM: homo sapiens

<400> SEQUENCE: 8

```
Met Val Ser Tyr Trp Asp Thr Gly Val Leu Leu Cys Ala Leu Leu Ser
 1               5                  10                 15

Cys Leu Leu Leu Thr Gly Ser Ser Gly Gly Arg Pro Phe Val Glu
            20              25              30

Met Tyr Ser Glu Ile Pro Glu Ile His Met Thr Glu Gly Arg Glu
        35              40              45

Leu Val Ile Pro Cys Arg Val Thr Ser Pro Asn Ile Thr Val Thr Leu
    50              55                  60

Lys Lys Phe Pro Leu Asp Thr Leu Ile Pro Asp Gly Lys Arg Ile Ile
 65              70                  75                  80

Trp Asp Ser Arg Lys Gly Phe Ile Ile Ser Asn Ala Thr Tyr Lys Glu
                85              90                  95

Ile Gly Leu Leu Thr Cys Glu Ala Thr Val Asn Gly His Leu Tyr Lys
            100             105             110

Thr Asn Tyr Leu Thr His Arg Gln Thr Asn Thr Ile Ile Asp Val Val
            115             120             125

Leu Ser Pro Ser His Gly Ile Glu Leu Ser Val Gly Glu Lys Leu Val
    130             135             140

Leu Asn Cys Thr Ala Arg Thr Glu Leu Asn Val Gly Ile Asp Phe Asn
145             150             155             160

Trp Glu Tyr Pro Ser Ser Lys His Gln His Lys Lys Leu Val Asn Arg
                165             170             175

Asp Leu Lys Thr Gln Ser Gly Ser Glu Met Lys Lys Phe Leu Ser Thr
            180             185             190

Leu Thr Ile Asp Gly Val Thr Arg Ser Asp Gln Gly Leu Tyr Thr Cys
            195             200             205

Ala Ala Ser Ser Gly Leu Met Thr Lys Lys Asn Ser Thr Phe Val Arg
    210             215             220

Val His Glu Lys Gly Pro Gly Asp Lys Thr His Thr Cys Pro Pro Cys
225             230             235             240

Pro Ala Pro Glu Leu Leu Gly Gly Pro Ser Val Phe Leu Phe Pro Pro
                245             250             255

Lys Pro Lys Asp Thr Leu Met Ile Ser Arg Thr Pro Glu Val Thr Cys
            260             265             270

Val Val Val Asp Val Ser His Glu Asp Pro Glu Val Lys Phe Asn Trp
            275             280             285

Tyr Val Asp Gly Val Glu Val His Asn Ala Lys Thr Lys Pro Arg Glu
    290             295             300

Glu Gln Tyr Asn Ser Thr Tyr Arg Val Val Ser Val Leu Thr Val Leu
305             310             315             320

His Gln Asp Trp Leu Asn Gly Lys Glu Tyr Lys Cys Lys Val Ser Asn
                325             330             335

Lys Ala Leu Pro Ala Pro Ile Glu Lys Thr Ile Ser Lys Ala Lys Gly
            340             345             350

Gln Pro Arg Glu Pro Gln Val Tyr Thr Leu Pro Pro Ser Arg Asp Glu
            355             360             365

Leu Thr Lys Asn Gln Val Ser Leu Thr Cys Leu Val Lys Gly Phe Tyr
    370             375             380

Pro Ser Asp Ile Ala Val Glu Trp Glu Ser Asn Gly Gln Pro Glu Asn
385             390             395             400

Asn Tyr Lys Thr Thr Pro Pro Val Leu Asp Ser Asp Gly Ser Phe Phe
                405             410             415
```

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
            435                 440                 445

Gln Lys Ser Leu Ser Leu Ser Pro Gly Lys
            450                 455

<210> SEQ ID NO 9
<211> LENGTH: 1377
<212> TYPE: DNA
<213> ORGANISM: homo sapiens

<400> SEQUENCE: 9

| | | | | | |
|---|---|---|---|---|---|
| atggtcagct | actgggacac | cggggtcctg | ctgtgcgcgc | tgctcagctg | tctgcttctc | 60 |
| acaggatcta | gttccggaag | tgataccggt | agacctttcg | tagagatgta | cagtgaaatc | 120 |
| cccgaaatta | tacacatgac | tgaaggaagg | gagctcgtca | ttccctgccg | ggttacgtca | 180 |
| cctaacatca | ctgttacttt | aaaaaagttt | ccacttgaca | ctttgatccc | tgatggaaaa | 240 |
| cgcataatct | gggacagtag | aaagggcttc | atcatatcaa | atgcaacgta | caaagaaata | 300 |
| ggcttctga | cctgtgaagc | aacagtcaat | gggcatttgt | ataagacaaa | ctatctcaca | 360 |
| catcgacaaa | ccaatacaat | catagatgtg | gttctgagtc | cgtctcatgg | aattgaacta | 420 |
| tctgttggag | aaaagcttgt | cttaaattgt | acagcaagaa | ctgaactaaa | tgtggggatt | 480 |
| gacttcaact | gggaataccc | ttcttcgaag | catcagcata | agaaacttgt | aaaccgagac | 540 |
| ctaaaaaccc | agtctgggag | tgagatgaag | aaatttttga | gcaccttaac | tatagatggt | 600 |
| gtaacccgga | gtgaccaagg | attgtacacc | tgtgcagcat | ccagtgggct | gatgaccaag | 660 |
| aagaacagca | catttgtcag | ggtccatgaa | aaggacaaaa | ctcacacatg | cccaccgtgc | 720 |
| ccagcacctg | aactcctggg | gggaccgtca | gtcttcctct | tccccccaaa | acccaaggac | 780 |
| accctcatga | tctcccggac | ccctgaggtc | acatgcgtgg | tggtggacgt | gagccacgaa | 840 |
| gaccctgagg | tcaagttcaa | ctggtacgtg | gacggcgtgg | aggtgcataa | tgccaagaca | 900 |
| aagccgcggg | aggagcagta | caacagcacg | taccgtgtgg | tcagcgtcct | caccgtcctg | 960 |
| caccaggact | ggctgaatgg | caaggagtac | aagtgcaagg | tctccaacaa | agccctccca | 1020 |
| gcccccatcg | agaaaaccat | ctccaaagcc | aaagggcagc | cccgagaacc | acaggtgtac | 1080 |
| accctgcccc | catcccggga | tgagctgacc | aagaaccagg | tcagcctgac | ctgcctggtc | 1140 |
| aaaggcttct | atcccagcga | catcgccgtg | gagtgggaga | gcaatgggca | gccggagaac | 1200 |
| aactacaaga | ccacgcctcc | cgtgctggac | tccgacggct | ccttcttcct | ctacagcaag | 1260 |
| ctcaccgtgg | acaagagcag | gtggcagcag | gggaacgtct | tctcatgctc | cgtgatgcat | 1320 |
| gaggctctgc | acaaccacta | cacgcagaag | agcctctccc | tgtctccggg | taaatga | 1377 |

<210> SEQ ID NO 10
<211> LENGTH: 458
<212> TYPE: PRT
<213> ORGANISM: homo sapiens

<400> SEQUENCE: 10

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
            35                  40                  45

```
Gly Arg Glu Leu Val Ile Pro Cys Arg Val Thr Ser Pro Asn Ile Thr
 50                  55                  60
Val Thr Leu Lys Lys Phe Pro Leu Asp Thr Leu Ile Pro Asp Gly Lys
 65                  70                  75                  80
Arg Ile Ile Trp Asp Ser Arg Lys Gly Phe Ile Ile Ser Asn Ala Thr
                     85                  90                  95
Tyr Lys Glu Ile Gly Leu Leu Thr Cys Glu Ala Thr Val Asn Gly His
                100                 105                 110
Leu Tyr Lys Thr Asn Tyr Leu Thr His Arg Gln Thr Asn Thr Ile Ile
            115                 120                 125
Asp Val Val Leu Ser Pro Ser His Gly Ile Glu Leu Ser Val Gly Glu
130                 135                 140
Lys Leu Val Leu Asn Cys Thr Ala Arg Thr Glu Leu Asn Val Gly Ile
145                 150                 155                 160
Asp Phe Asn Trp Glu Tyr Pro Ser Ser Lys His Gln His Lys Lys Leu
                165                 170                 175
Val Asn Arg Asp Leu Lys Thr Gln Ser Gly Ser Glu Met Lys Lys Phe
            180                 185                 190
Leu Ser Thr Leu Thr Ile Asp Gly Val Thr Arg Ser Asp Gln Gly Leu
            195                 200                 205
Tyr Thr Cys Ala Ala Ser Ser Gly Leu Met Thr Lys Lys Asn Ser Thr
210                 215                 220
Phe Val Arg Val His Glu Lys Asp Lys Thr His Thr Cys Pro Pro Cys
225                 230                 235                 240
Pro Ala Pro Glu Leu Leu Gly Gly Pro Ser Val Phe Leu Phe Pro Pro
                245                 250                 255
Lys Pro Lys Asp Thr Leu Met Ile Ser Arg Thr Pro Glu Val Thr Cys
            260                 265                 270
Val Val Val Asp Val Ser His Glu Asp Pro Glu Val Lys Phe Asn Trp
            275                 280                 285
Tyr Val Asp Gly Val Glu Val His Asn Ala Lys Thr Lys Pro Arg Glu
290                 295                 300
Glu Gln Tyr Asn Ser Thr Tyr Arg Val Val Ser Val Leu Thr Val Leu
305                 310                 315                 320
His Gln Asp Trp Leu Asn Gly Lys Glu Tyr Lys Cys Lys Val Ser Asn
                325                 330                 335
Lys Ala Leu Pro Ala Pro Ile Glu Lys Thr Ile Ser Lys Ala Lys Gly
            340                 345                 350
Gln Pro Arg Glu Pro Gln Val Tyr Thr Leu Pro Pro Ser Arg Asp Glu
            355                 360                 365
Leu Thr Lys Asn Gln Val Ser Leu Thr Cys Leu Val Lys Gly Phe Tyr
            370                 375                 380
Pro Ser Asp Ile Ala Val Glu Trp Glu Ser Asn Gly Gln Pro Glu Asn
385                 390                 395                 400
Asn Tyr Lys Thr Thr Pro Pro Val Leu Asp Ser Asp Gly Ser Phe Phe
                405                 410                 415
Leu Tyr Ser Lys Leu Thr Val Asp Lys Ser Arg Trp Gln Gln Gly Asn
            420                 425                 430
Val Phe Ser Cys Ser Val Met His Glu Ala Leu His Asn His Tyr Thr
            435                 440                 445
Gln Lys Ser Leu Ser Leu Ser Pro Gly Lys
450                 455
```

```
<210> SEQ ID NO 11
<211> LENGTH: 4
<212> TYPE: PRT
<213> ORGANISM: homo sapiens
<220> FEATURE:
<221> NAME/KEY: VARIANT
<222> LOCATION: 1, 2, 3, 4
<223> OTHER INFORMATION: Xaa = Any Amino Acid

<400> SEQUENCE: 11

Xaa Xaa Xaa Xaa
 1

<210> SEQ ID NO 12
<211> LENGTH: 1444
<212> TYPE: DNA
<213> ORGANISM: homo sapiens

<400> SEQUENCE: 12
aagcttgggc tgcaggtcga tcgactctag aggatcgatc cccgggcgag ctcgaattcg      60
caaccaccat ggtcagctac tgggacaccg gggtcctgct gtgcgcgctg ctcagctgtc     120
tgcttctcac aggatctagt tccggaggta gacctttcgt agagatgtac agtgaaatcc     180
ccgaaattat acacatgact gaaggaaggg agctcgtcat tccctgccgg ttacgtcac      240 ctaacatcac tgttactta aaaagtttc cacttgacac tttgatccct gatggaaaac       300
gcataatctg ggacagtaga aagggcttca tcatatcaaa tgcaacgtac aaagaaatag     360
ggcttctgac ctgtgaagca acagtcaatg gcatttgta taagacaaac tatctcacac      420
atcgacaaac caatacaatc atagatatcc agctgttgcc caggaagtcg ctggagctgc     480
tggtagggga aagctggtc ctcaactgca ccgtgtgggc tgagtttaac tcaggtgtca      540
cctttgactg ggactaccca gggaagcagg cagagcgggg taagtgggtg cccgagcgac     600
gctcccaaca gacccacaca gaactctcca gcatcctgac catccacaac gtcagccagc     660
acgacctggg ctcgtatgtg tgcaaggcca acaacggcat ccagcgattt cgggagagca     720
ccgaggtcat tgtgcatgaa aatgcccgg gcgacaaaac tcacacatgc ccaccgtgcc     780
cagcacctga actcctgggg ggaccgtcag tcttcctctt ccccccaaaa cccaaggaca     840
ccctcatgat ctcccggacc cctgaggtca catgcgtggt ggtggacgtg agccacgaag     900
accctgaggt caagttcaac tggtacgtgg acggcgtgga ggtgcataat gccaagacaa     960
agccgcggga ggagcagtac aacagcacgt accgtgtggt cagcgtcctc accgtcctgc    1020
accaggactg gctgaatggc aaggagtaca agtgcaaggt ctccaacaaa gccctcccag    1080
cccccatcga gaaaaccatc tccaaagcca agggcagcc cgagaaccag gtgtacaca    1140 ccctgccccc atcccgggat gagctgacca agaaccaggt cagcctgacc tgcctggtca    1200
aaggcttcta tcccagcgac atcgccgtgg agtgggagag caatgggcag ccggagaaca    1260
actacaagac cacgcctccc gtgctggact ccgacggctc cttcttcctc tatagcaagc    1320
tcaccgtgga caagagcagg tggcagcagg ggaacgtctt ctcatgctcc gtgatgcatg    1380
aggctctgca caaccactac acgcagaaga gcctctccct gtctccgggt aaatgagcgg    1440
ccgc                                                                  1444

<210> SEQ ID NO 13
<211> LENGTH: 455
<212> TYPE: PRT
<213> ORGANISM: homo sapiens
```

<400> SEQUENCE: 13

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Gly Arg Pro Phe Val Glu
             20                  25                  30

Met Tyr Ser Glu Ile Pro Glu Ile Ile His Met Thr Glu Gly Arg Glu
         35                  40                  45

Leu Val Ile Pro Cys Arg Val Thr Ser Pro Asn Ile Thr Val Thr Leu
     50                  55                  60

Lys Lys Phe Pro Leu Asp Thr Leu Ile Pro Asp Gly Lys Arg Ile Ile
 65                  70                  75                  80

Trp Asp Ser Arg Lys Gly Phe Ile Ile Ser Asn Ala Thr Tyr Lys Glu
                 85                  90                  95

Ile Gly Leu Leu Thr Cys Glu Ala Thr Val Asn Gly His Leu Tyr Lys
            100                 105                 110

Thr Asn Tyr Leu Thr His Arg Gln Thr Asn Thr Ile Ile Asp Ile Gln
        115                 120                 125

Leu Leu Pro Arg Lys Ser Leu Glu Leu Leu Val Gly Glu Lys Leu Val
130                 135                 140

Leu Asn Cys Thr Val Trp Ala Glu Phe Asn Ser Gly Val Thr Phe Asp
145                 150                 155                 160

Trp Asp Tyr Pro Gly Lys Gln Ala Glu Arg Gly Lys Trp Val Pro Glu
                165                 170                 175

Arg Arg Ser Gln Gln Thr His Thr Glu Leu Ser Ser Ile Leu Thr Ile
            180                 185                 190

His Asn Val Ser Gln His Asp Leu Gly Ser Tyr Val Cys Lys Ala Asn
        195                 200                 205

Asn Gly Ile Gln Arg Phe Arg Glu Ser Thr Glu Val Ile Val His Glu
    210                 215                 220

Asn Gly Pro Gly Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415
```

Lys Leu Thr Val Asp Lys Ser Arg Trp Gln Gln Gly Asn Val Phe Ser
    420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 14
<211> LENGTH: 24
<212> TYPE: DNA
<213> ORGANISM: homo sapiens

<400> SEQUENCE: 14
gggctgttga gagagagaga gagc                                     24

<210> SEQ ID NO 15
<211> LENGTH: 28
<212> TYPE: DNA
<213> ORGANISM: homo sapiens

<400> SEQUENCE: 15
ggccgctctc tctctctctc aacagccc                                 28

<210> SEQ ID NO 16
<211> LENGTH: 23
<212> TYPE: DNA
<213> ORGANISM: homo sapiens

<400> SEQUENCE: 16
gggcgcatgc ggttgttgag agc                                      23

<210> SEQ ID NO 17
<211> LENGTH: 27
<212> TYPE: DNA
<213> ORGANISM: homo sapiens

<400> SEQUENCE: 17
ggccgctctc aacaaccgca tgcgccc                                  27

<210> SEQ ID NO 18
<211> LENGTH: 36
<212> TYPE: DNA
<213> ORGANISM: homo sapiens

<400> SEQUENCE: 18
gagagagacc atgggtagac ctttcgtaga gatgta                        36

<210> SEQ ID NO 19
<211> LENGTH: 48
<212> TYPE: DNA
<213> ORGANISM: homo sapiens

<400> SEQUENCE: 19
agagaggcgg ccgctttatc aacactttc atggaccctg acaaatgt            48

<210> SEQ ID NO 20
<211> LENGTH: 57
<212> TYPE: DNA
<213> ORGANISM: homo sapiens

<400> SEQUENCE: 20
agagaggcgg ccgctttatc aacaaccgca tgccttttca tggaccctga caaatgt  57

<210> SEQ ID NO 21
<211> LENGTH: 39
<212> TYPE: DNA
<213> ORGANISM: homo sapiens

<400> SEQUENCE: 21
agttccggaa gtgccatggg tagacctttc gtagagatg                    39

<210> SEQ ID NO 22
<211> LENGTH: 44
<212> TYPE: DNA
<213> ORGANISM: homo sapiens

<400> SEQUENCE: 22
agagaggcgg ccgctgttat cacttctcgt gcacgcgcac gaag              44

<210> SEQ ID NO 23
<211> LENGTH: 232
<212> TYPE: PRT
<213> ORGANISM: homo sapiens

<400> SEQUENCE: 23

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Thr Gln Ser Gly Ser Glu Met Lys Arg Asp Leu Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Cys
225                 230

<210> SEQ ID NO 24
<211> LENGTH: 435
<212> TYPE: PRT
<213> ORGANISM: homo sapiens

<400> SEQUENCE: 24

```
Met Val Ser Tyr Trp Asp Thr Gly Val Leu Leu Cys Ala Leu Leu Ser
 1               5                  10                  15
Cys Leu Leu Thr Gly Ser Ser Gly Ser Asp Thr Gly Arg Pro
             20                  25                  30
Phe Val Glu Met Tyr Ser Glu Ile Pro Glu Ile Ile His Met Thr Glu
             35                  40                  45
Gly Arg Glu Leu Val Ile Pro Cys Arg Val Thr Ser Pro Asn Ile Thr
 50                  55                  60
Val Thr Leu Lys Lys Phe Pro Leu Asp Thr Leu Ile Pro Asp Gly Lys
 65                  70                  75                  80
Arg Ile Ile Trp Asp Ser Arg Lys Gly Phe Ile Ile Ser Asn Ala Thr
                 85                  90                  95
Tyr Lys Glu Ile Gly Leu Leu Thr Cys Glu Ala Thr Val Asn Gly His
                100                 105                 110
Leu Tyr Lys Thr Asn Tyr Leu Thr His Arg Gln Thr Asn Thr Ile Ile
            115                 120                 125
Asp Val Val Leu Ser Pro Ser His Gly Ile Glu Leu Ser Val Gly Glu
130                 135                 140
Lys Leu Val Leu Asn Cys Thr Ala Arg Thr Glu Leu Asn Val Gly Ile
145                 150                 155                 160
Asp Phe Asn Trp Glu Tyr Pro Ser Ser Lys His Gln His Lys Lys Leu
                165                 170                 175
Val Asn Arg Asp Leu Lys Thr Gln Ser Gly Ser Glu Met Lys Lys Phe
            180                 185                 190
Leu Ser Thr Leu Thr Ile Asp Gly Val Thr Arg Ser Asp Gln Gly Leu
            195                 200                 205
Tyr Thr Cys Ala Ala Ser Ser Gly Leu Met Thr Lys Lys Asn Ser Thr
210                 215                 220
Phe Val Arg Val His Glu Lys Gly Pro Gly Arg Pro Phe Val Glu Met
225                 230                 235                 240
Tyr Ser Glu Ile Pro Glu Ile Ile His Met Thr Glu Gly Arg Glu Leu
                245                 250                 255
Val Ile Pro Cys Arg Val Thr Ser Pro Asn Ile Thr Val Thr Leu Lys
            260                 265                 270
Lys Phe Pro Leu Asp Thr Leu Ile Pro Asp Gly Lys Arg Ile Ile Trp
            275                 280                 285
Asp Ser Arg Lys Gly Phe Ile Ile Ser Asn Ala Thr Tyr Lys Glu Ile
290                 295                 300
Gly Leu Leu Thr Cys Glu Ala Thr Val Asn Gly His Leu Tyr Lys Thr
305                 310                 315                 320
Asn Tyr Leu Thr His Arg Gln Thr Asn Thr Ile Ile Asp Val Val Leu
                325                 330                 335
Ser Pro Ser His Gly Ile Glu Leu Ser Val Gly Glu Lys Leu Val Leu
            340                 345                 350
Asn Cys Thr Ala Arg Thr Glu Leu Asn Val Gly Ile Asp Phe Asn Trp
            355                 360                 365
Glu Tyr Pro Ser Ser Lys His Gln His Lys Lys Leu Val Asn Arg Asp
            370                 375                 380
Leu Lys Thr Gln Ser Gly Ser Glu Met Lys Lys Phe Leu Ser Thr Leu
385                 390                 395                 400
Thr Ile Asp Gly Val Thr Arg Ser Asp Gln Gly Leu Tyr Thr Cys Ala
```

-continued

```
                       405                 410                 415
Ala Ser Ser Gly Leu Met Thr Lys Lys Asn Ser Thr Phe Val Arg Val
                420                 425                 430

His Glu Lys
        435

<210> SEQ ID NO 25
<211> LENGTH: 235
<212> TYPE: PRT
<213> ORGANISM: homo sapiens

<400> SEQUENCE: 25

Met Val Ser Tyr Trp Asp Thr Gly Val Leu Leu Cys Ala Leu Leu Ser
  1               5                  10                  15

Cys Leu Leu Leu Thr Gly Ser Ser Ser Gly Ser Asp Thr Gly Arg Pro
                 20                  25                  30

Phe Val Glu Met Tyr Ser Glu Ile Pro Glu Ile Ile His Met Thr Glu
                 35                  40                  45

Gly Arg Glu Leu Val Ile Pro Cys Arg Val Thr Ser Pro Asn Ile Thr
 50                  55                  60

Val Thr Leu Lys Lys Phe Pro Leu Asn Thr Leu Ile Pro Asn Gly Lys
 65                  70                  75                  80

Ala Ile Ile Trp Asp Ser Arg Lys Gly Phe Ile Ile Ser Asn Ala Thr
                 85                  90                  95

Tyr Lys Glu Ile Gly Leu Leu Thr Cys Glu Ala Thr Val Asn Gly His
                100                 105                 110

Leu Tyr Lys Thr Asn Tyr Leu Thr His Arg Gln Thr Asn Thr Ile Ile
                115                 120                 125

Asp Val Val Leu Ser Pro Ser His Gly Ile Glu Leu Ser Val Gly Glu
                130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
                180                 185                 190

Leu Ser Thr Leu Thr Ile Asp Gly Val Thr Arg Ser Asp Gln Gly Leu
                195                 200                 205

Tyr Thr Cys Ala Ala Ser Ser Gly Leu Met Thr Lys Lys Asn Ser Thr
                210                 215                 220

Phe Val Arg Val His Glu Lys Ala Cys Gly Cys
225                 230                 235
```